United States Patent [19]

Hill

[11] 4,142,522

[45] * Mar. 6, 1979

[54] PEDIATRIC ARM RESTRAINT AND METHOD OF USING SAME

[75] Inventor: Edward J. Hill, Detroit, Mich.

[73] Assignee: H & H Research, Inc., Bloomfield Township, Oakland County, Mich.

[*] Notice: The portion of the term of this patent subsequent to Mar. 14, 1995, has been disclaimed.

[21] Appl. No.: 834,689

[22] Filed: Sep. 19, 1977

Related U.S. Application Data

[63] Continuation-in-part of Ser. No. 711,496, Aug. 4, 1976, Pat. No. 4,078,560.

[51] Int. Cl.² .................................................. A61F 13/00
[52] U.S. Cl. ...................................................... 128/133
[58] Field of Search .................................... 128/132–135

[56] References Cited

U.S. PATENT DOCUMENTS

| | | | |
|---|---|---|---|
| 1,623,125 | 4/1927 | Levine | 128/133 |
| 1,638,601 | 8/1927 | Stanciu | 128/133 |
| 2,843,118 | 7/1958 | Pelow | 128/133 |
| 2,998,008 | 8/1961 | Klesa | 128/133 |
| 3,008,466 | 11/1961 | Adam | 128/133 |
| 3,010,452 | 11/1961 | Smith | 128/133 |
| 3,297,026 | 1/1967 | Van Pelt | 128/133 |

*Primary Examiner*—Lawrence W. Trapp
*Attorney, Agent, or Firm*—Arnold, White & Durkee

[57] ABSTRACT

A pediatric arm restraint is disclosed for restricting movement of an infant's arm at the elbow. The restraint includes an inner foam pad and an outer stiff rigidifying plastic sheet, the foam pad preferably being the larger of these two components to extend beyond the edges of the plastic sheet for comfort to the infant. Both the pad and the sheet taper from a major edge to a minor edge to facilitate forming the restraint into a conical shape for use, with the major edge being adapted for placement in an infant's axilla and the minor edge fitting below the infant's elbow. The restraint is normally flat for ease in shipping and handling, but is easily bent into a generally tubular configuration, preferably a tubular-conical configuration, around an infant's arm and then secured in that position by Velcro strips.

11 Claims, 2 Drawing Figures

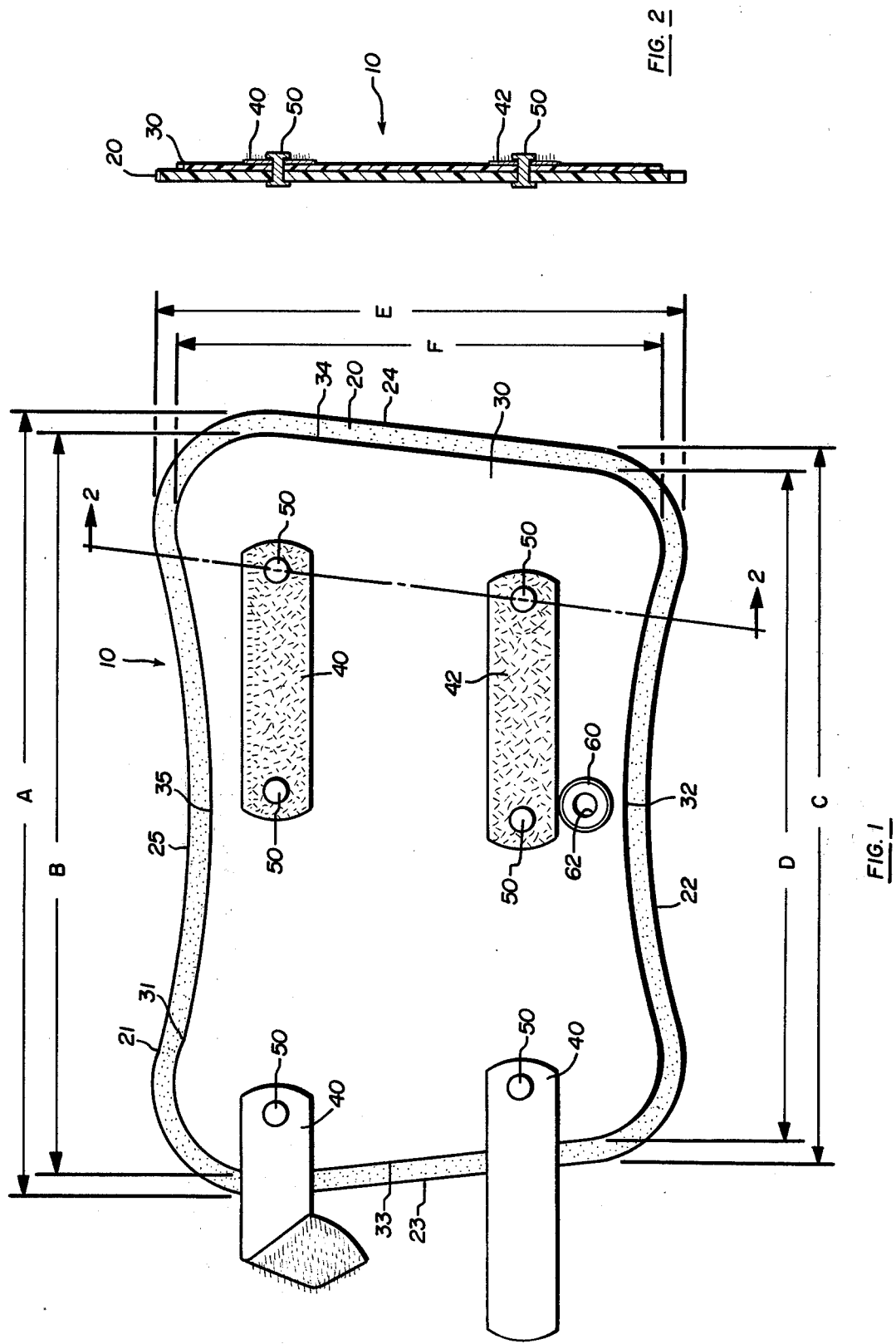

PEDIATRIC ARM RESTRAINT AND METHOD OF USING SAME

CROSS-REFERENCE TO RELATED APPLICATION

This application is a continuation-in-part of application Ser. No. 711,496, filed Aug. 4, 1976, now U.S. Pat. No. 4,078,560 issued Mar. 14, 1978.

BACKGROUND OF THE INVENTION

1. Field of the Invention

This invention relates generally to an arm restraint, and more particularly to a light weight, durable, comfortable, and disposable pediatric arm restraint.

2. The Prior Art

Pediatricians and hospital personnel have long been confronted with the problem of restricting an infant's hands following surgery or during an intravenous feeding. Infants, by their natural curious nature, always try to pull at intravenous feedings tubes or medical dressings, thereby drastically reducing their effectiveness and requiring further medical attention.

Various prior attempts have been made to solve this problem, but no truly successful remedies have heretofore emerged.

One such attempt included merely placing a sock over the infant's hands and arms. This, however, is not truly effective and desirable because the sock is easily removed and because the infant is unable to use its hands for permissive activity while the sock is on the arm.

A second attempt included the use of splints and gauze wrapping to keep the elbow straight, but this technique is both time consuming to the pediatrician and relatively uncomfortable to the young patient.

A third attempt involves the use of two semicylindrical medical metal frames which are placed around the infant's arm and taped in place to keep the elbow straight. Likewise, this particular effort has proved to be undesirable because (1) the end of the metal frames irritate the infant's axilla region, (2) the frames are heavy, particularly to the young patient, and (3) this device is relatively expensive.

A fourth attempt involves the use of two plastic sheets secured together by an adhesive, as shown by U.S. Pat. No. 3,008,466. This particular device, however, does not totally restrict elbow movement by virtue of the hinge established by the adhesive.

Other prior art restraining devices are shown by U.S. Pat. Nos. 2,998,008, 3,297,026, and 3,010,452.

Most notably, none of the prior art devices provide a tapering or conical feature which accomodates the reducing size of the arm from the shoulder to the hand.

In short, no suitable prior art device restricts the movement of an infant's elbow while also permitting free use of the infant's hands.

SUMMARY OF THE INVENTION

These prior art problems are eliminated by the present invention, which relates to a pediatric arm restraint that is shaped to facilitate its formation into a conical configuration during use.

Most preferably, the restraint includes an inner foam pad affixed to an outer, overlying and rigidifying plastic sheet that can be wrapped into tubular form to cover the entire arm and then secured into position. The inner foam pad, which is essentially rectangular and relatively thin, is placed against the infant's arm to provide a non-irritating cushion. The plastic sheet is likewise essentially rectangular, but is flexible and deformable, yet relatively stiff in order to stiffen and rigify the arm restraint, particularly when wrapped around the patient's arm in tubular conical form.

To facilitate the formation of the conical shape, the pad and sheet taper form a first edge through converging lateral edges to a second edge. The first edge is larger for placement adjacent the axilla region, with the second edge being smaller for wrapping around the smaller portion of the arm below the elbow.

The foam pad and the plastic sheet are secured to one another in overlying, generally aligned manner, with the foam pad preferably being dimensioned to extend beyond the outer lateral edges of the plastic sheet to provide cushion protection from those edges. One edge of the arm restraint preferably includes an arcuate indented, concave contour to provide a curved edge for placement in the axilla of the infant. Securing means are also preferably carried by the plastic sheet for releasably maintaining the arm restraint in the tubular, wrapped position to restrict the arm movement at the elbow over the desired period of time.

In the preferred embodiment, both the foam pad and the plastic sheet include respective, aligned, generally arcuate indentations along one of their corresponding, respective edges to provide the curved edge on the body portion.

Additionally, the securing means in the preferred embodiment is comprised of two or more pairs of cooperating, complementary Velcro strips secured to the outer surface of the plastic sheet by rivets. One strip in each of the pairs is secured by rivets at each of their ends at a position which is completely in the boundary formed by the edges of the plastic strip. The other strip in each of those pairs is secured to the plastic sheet adjacent one of its edges so that those strips extend beyond the edge to overlap and interlock with the other of the strips when the arm restraint is wrapped around the patient's arm. In this preferred arrangement, the rivets extend through the Velcro strips, the plastic sheet and the foam pad to provide a dual purpose—to secure the Velcro strips to the body portion of the arm restraint and to secure the foam pad to the plastic sheet.

An optional opening may be provided through the body portion of the restraint for receiving a cord which can be attached to a fixture, such as a bedpost, to restrain the movement of the infant's arm at the shoulder.

The method of using the invention includes bending the arm restraint from its initial, essentially flat shape into an essentially tubular conical shape to cover the infant's arm from the axilla to the wrist, with the larger edge of the body portion being placed within the axilla region. Then, the arm restraint is secured in the tubular conical position by suitable securement means to provide prolonged restraint of movement to the elbow. During use, the restraint prevents the infant patient from bending its elbows, and therefore prevents the infant from placing its hands in prohibited regions. Eventually, the arm restraint is removed from the infant's arm by releasing the securing means and then bending the arm restraint from the generally tubular conical configuration.

Accordingly, the present invention provides the following desirable advantages which have heretofore been missing in the prior art. First, the present pediatric arm restraint is light weight and comfortable as a result of the overall design and selection of materials. The arm restraint is also inexpensive and may therefore be disposed of after use with a particular patient. Equally as important, the present arm restraint is easy to use, both in placement around the patient's arm and in its removal. Yet another advantage is that this restraint in non-irritating to the infant patient and allows free use of the hands for permissible activity, such as holding toys. Additionally, the arm restraint of this disclosure is shaped and dimensioned to facilitate bending the restraint into a conical configuration during use.

These and other meritorious features and advantages will become more apparent from the following detailed description of the pediatric arm restraint and from the appended claims.

BRIEF DESCRIPTION OF THE DRAWINGS

FIG. 1 is a frontal view of the pediatric arm restraint, in generally flat configuration prior to being placed around a patient's arm.

FIG. 2 is a cross-sectional view of the arm restraint, taken along plane 2—2 of FIG. 1.

DETAILED DESCRIPTION OF THE PREFERRED EMBODIMENT

Referring now more particularly to the drawings, the pediatric arm restraint of this invention is shown by reference numeral 10 in a generally flat position in FIG. 1 prior to being placed in use on a patient's arm. The general positioning of the arm restraint in use is shown in the drawing for parent application Ser. No. 711,496, which is incorporated by reference. The primary difference between the present disclosure and that of Ser. No. 711,496 relates to the tapering feature of the arm restraint in order to facilitate bending the restraint into a conical shape during use.

The arm restraint 10 includes a quadrilateral, generally rectangular, cushion pad 20 which is interconnected to a quadrilateral, generally rectangular, rigidifying cuff 30. Both the pad 20 and sheet 30 also have generally an overall trapezoidal shape. As illustrated, the trapezoidal shape of the foam pad is defined by a top major edge 21, a lower edge 22, and converging lateral side edges 23 and 24. Likewise, the trapezoidal shape of the cuff is defined by a top major edge 31, a lower edge 32, and converging sides 33 and 34. This overall configuration is conducive to forming the arm restraint into generally a conical tubular configuration during use so that the diameter of the tubular, wrapped restraint diminishes generally in the same manner that the arm reduces in size from the shoulder to the hand.

As illustrated, the cushion pad is preferably at least slightly larger than the cuff in order to provide a cushioning border so that the edges of the rigidifying cuff will be spaced from the user's skin to prevent irritation. Any suitable soft cushion material may be used for the cushion pad 20 such as foam rubber. In the preferred embodiment, a sheet of polyethylene foam is proposed, such as that sold under the trade name Ethafoam by Dow Chemical Co. Likewise, the rigidifying cuff may be comprised of any suitable material which is flexible and deformable, yet stiff for providing the desired arm restraint. A specific example of such a material is polypropylene. As illustrated in FIG. 2, the foam pad is preferably thicker than the cuff, suitable thicknesses being about one-eighth of an inch for the pad 20 and one-sixty-fourth of an inch for the cuff 30.

As can be seen from FIG. 1, the arm restraint 10 includes a top contoured region in the form of an arcuate depression, which is designed for fitting within the axilla (i.e. arm pit) of an infant. This concave contour is reflected in the pad 20 by an indentation 25 and in the cuff 30 by a similar indentation 35.

Additionally, the arm restraint 10 preferably includes a bottom contoured region in the form of an arcuate depression to facilitate forming the device into a conical configuration. This depression is reflected in the pad 20 as a depression along lower edge 22 and in the cuff 30 as a similar depression along lower edge 32.

Two sets of cooperating attachment straps 40 and 42, which is the disclosed embodiment are straps sold under the trade name Velcro, are suitably secured to the arm restraint 10 to serve as securing means to maintain the arm restraint in the generally conical tubular restraining position when in use. In the preferred embodiment, the Velcro straps are secured to the arm restraint by rivets 50, which extend through the straps, the rigidifying cuff 30 and the cushion pad 12, as illustrated in FIG. 2. Thus, the rivets serve two purposes; first they secure the Velcro straps to the arm restraint and secondly, they secure the rigidifying cuff and the cushion pad to each other.

To use the arm restraint 10, a pediatrician or other medical personnel simply needs to wrap the arm restraint around the infant's arm and interlock the Velcro straps. Ideally, the arm restraint should be dimensioned so that it extends substantially from the shoulder region to the wrist to provide the necessary restraining support to the arm to prevent the infant from bending its elbow, thus preventing the infant from placing its hands in restricted regions. Accordingly, in the method of use the contoured region 25 of pad 20 will be placed in the axilla and the other end of the arm restraint will extend below the elbow to substantially the wrist. Next, about one half of the restraint is bent to wrap around part of the patient's arm and then the other half of the restraint is bent to wrap around the other part of the patient's arm and to overlap with part of the first bent portion. The converging sides of the arm restraint facilitaes forming the restraint into generally a conical tubular shape to closely receive the arm along the length of the arm. Finally, the restraint is secured into position by suitable means, such as by the disclosed Velcro straps 40 and 42.

Naturally, different sized arm restraints 10 may be made to accommodate different aged and different sized pediatric patients. For example, the dimensions for typical arm restraints for three different categories of patients are provided below in reference to FIG. 1.

| Dimension | "NEWBORN" | "INFANT" | "CHILDREN" |
|---|---|---|---|
| A | 8" | 9" | 10¼" |
| B | 7¼" | 8¼" | 10" |
| C | 6⅝" | 7¾" | 8¾" |
| D | 6⅛" | 7⅛" | 8¼" |
| E | 5½" | 7" | 8⅝" |
| F | 5" | 6½" | 8⅛" |

Thus, it can be seen that the restraint tapers from dimensions "A" and "B" to dimensions "C" and "D," respectively, to facilitate the conical shape in use. It can also be seen that the difference between dimensions "A" and "B," between "C" and "D," and between "E" and "F" are approximately ½ inch, providing a cushion border all the way around the regidifying cuff 30 of approximately ¼ inch. Of course, these dimensions may be modified as desired.

An optional feature is shown by reference numeral 60, which includes an enlarged rivet providing an opening 62. In the event that it is desirable to completely restrain movement of the infant's arm, a cord can be inserted through opening 62 and appropriately tied to a fixture, such as a bed post. In this situation, the arm restraint prevents movement of the elbow, and the cord will prevent movement of the arm at the shoulder.

Thus, it is apparent that the present arm restraint provides numerous advantages, which have been elaborated on in earlier portions of this disclosure. Additionally, it is to be understood that this disclosure is exemplary in nature and limited only by the following appended claims. Various modifications may be made to the disclosure without departing from the inventive concept, such as employing three sets of Velcro straps in larger sizes.

Having therefore completely and sufficiently disclosed my invention, I now claim:

1. A pediatric arm restraint for wrapping around a child's arm to maintain the elbow straight so that the child is unable to place its hand on restricted regions, such as intravenous feedings or medical dressings, comprising:
   a quadrilateral body portion which is normally flat for shipping and deformable for wrapping completely around a child's arm to form an essentially tubular elbow restraint, with the body portion being adapted to extend from the child's axilla to below the elbow essentially to the wrist yet permitting freedom of movement of the arm at the shoulder and freedom of movement at the fingers and wrist, and the restraint including a first edge for placement in the child's axilla, a pair of laterally spaced edges converging from said first edge, and a second edge which is smaller than said first edge;
   the body portion including (a) an inner pad of relatively thin foam material for placement against the infant's arm to provide a non-irritating cushion and (b) a sheet of flexible, deformable, yet relatively stiff plastic material for rigidifying the arm restraint, the foam pad and the plastic sheet being interconnected in overlying generally aligned manner; and
   securing means carried by the plastic sheet for releasably maintaining the arm restraint in an essentially tubular wrapped position around the child's arm.

2. The arm restraint as defined in claim 1, wherein the foam pad is slightly larger than the plastic sheet and extends laterally beyond the periphery of the plastic sheet to provide a cushion protection from the sheet edges.

3. The arm restraint as defined in claim 2, wherein the foam pad includes a concave contour along an edge for placement within the child's axilla.

4. The arm restraint defined in claim 3, wherein the plastic sheet includes a concave contour along one of its edges adjacent the concave contour on the foam pad.

5. The arm restraint defined in claim 1, characterized by securing means being comprised of two pairs of cooperating, complementary Velcro strips, one strip of each of said pairs being secured to the outer surface of the plastic sheets by rivets and being positioned completely within the boundary formed by the edges of the plastic sheet, the other strip of each of said pairs being secured to the outer surface of the plastic sheet by a respective single rivet adjacent one lateral converging edge of the restraint so that the said other strips extend beyond one edge of the arm restraint to permit their overlapping and interlocking with the said one strip in said pairs when the arm restraint is wrapped around the patient's arm, and said rivets extending through the Velcro strips, the plastic sheet and the foam pad (a) to secure the Velcro strips to the body portion of the arm restraint and (b) to secure the foam pad to the plastic sheet.

6. The arm restraint as defined in claim 5, characterized by said foam pad being comprised of polyethylene foam and said plastic sheet being comprised of polypropylene.

7. An arm restraint, comprising:
   a normally flat, relatively thin pad of soft material for placement against the arm to provide a cushion, the pad having a first edge for placement above the elbow, a second edge for placement below the elbow and a pair of converging edges extending between the first and second edges, said first edge being larger than said second edge to accommodate the formation of an essentially conical configuration with the arm restraint is plced on a patient's arm;
   a thin sheet of flexible, deformable, yet relatively stiff material overlying and being secured to said pad, the sheet having essentially the same configuration as the pad but being slightly smaller so that the pad extends laterally beyond the periphery of the sheet to provide a cushion protection; and
   securement means carried by the sheet for releasably maintaining the arm restraint in an essentially conical configuration when in use.

8. The arm restraint as defined in claim 7, wherein the pad and sheet include a concave contour along their respective first edges to accommodate placement of the first edge in the axilla of a patient.

9. In a method of securing an arm restraint around a child's arm to prevent movement of the arm at the elbow, the steps of:
   (1) positioning an arm restraint in a child's axilla, the restraint having four sides and including (a) a relatively thin foam material placed against the child's arm to provide a non-irritating cushion and (b) a relatively thin sheet of flexible, deformable, yet relatively stiff plastic material for rigidifying the restraint; the foam pad and the plastic sheet being interconnected and overlying in generally aligned manner; the side of the restraint placed in the axilla being the major side of the restraint, the side opposite the major side being spaced sufficiently to be positioned below the elbow of the child, and the other two sides converging from the major side to the opposite side;
   (2) bending approximately one-half of the restraint around a portion of the child's arm and then bending approximately the other half of the restraint around the remaining portion of the child's arm to overlap the end portions of the restraint adjacent the converging sides, and thereby forming the restraint into essentially a conical shape which is larger at the axilla and smaller beneath the child's elbow; and then
   (3) securing the restraint in the conical shape to provide prolonged restraint to movement to the child's elbow.

10. The method as defined in claim 9 wherein the major side of the restraint includes a concave contour, characterized in Step (1) by placing the contour into the child's axilla.

11. The method as defined in claim 9, wherein the arm restraint includes two pairs of cooperating Velcro secured thereto, characterized in Step (3) by overlapping each pair of cooperating Velcro to secure the restraint in place.

* * * * *

UNITED STATES PATENT AND TRADEMARK OFFICE
CERTIFICATE OF CORRECTION

PATENT NO. : 4,142,522
DATED : March 6, 1979
INVENTOR(S) : Edward J. Hill

It is certified that error appears in the above-identified patent and that said Letters Patent are hereby corrected as shown below:

Column 1, line 31, delete "permissive" and insert
--Permissible--.
Column 4, line 14, delete "is" and insert --in--;
line 42, delete "faciltaes" and insert
--facilitates--.
Column 5, line 62, after "by" insert --said--.
Column 6, line 25, delete "with" and insert --when--;
line 25, delete "plced" and insert --placed--.

Signed and Sealed this

Thirteenth Day of November 1979

[SEAL]

Attest:

RUTH C. MASON
Attesting Officer

LUTRELLE F. PARKER
Acting Commissioner of Patents and Trademarks